US008153430B2

(12) United States Patent
Palladino et al.

(10) Patent No.: US 8,153,430 B2
(45) Date of Patent: Apr. 10, 2012

(54) METHODS RELATED TO SURGERY

(75) Inventors: Linda O. Palladino, Stormville, NY (US); Diana L. Clarke, Pittsburgh, PA (US); Vivienne S. Marshall, Glenshaw, PA (US); Charlotte A. Smith, Wexford, PA (US); Martin C. Robson, Stuart, FL (US)

(73) Assignee: Stemnion, Inc., Pittsburgh, PA (US)

( * ) Notice: Subject to any disclaimer, the term of this patent is extended or adjusted under 35 U.S.C. 154(b) by 813 days.

(21) Appl. No.: 12/217,259

(22) Filed: Jul. 2, 2008

(65) Prior Publication Data
US 2009/0010899 A1 Jan. 8, 2009

Related U.S. Application Data

(60) Provisional application No. 60/958,376, filed on Jul. 5, 2007, provisional application No. 60/666,949, filed on Mar. 31, 2005, provisional application No. 60/699,257, filed on Jul. 14, 2005, provisional application No. 60/742,067, filed on Dec. 2, 2005.

(51) Int. Cl.
*C12N 5/02* (2006.01)

(52) U.S. Cl. ............... 435/405; 435/325; 435/404

(58) Field of Classification Search .................. None
See application file for complete search history.

(56) References Cited

U.S. PATENT DOCUMENTS

| 4,361,552 | A | 11/1982 | Baur, Jr. | |
| 7,045,148 | B2 | 5/2006 | Hariri | |
| 7,118,746 | B1 * | 10/2006 | Naughton et al. | 424/184.1 |
| 2003/0032179 | A1 | 2/2003 | Hariri | |
| 2003/0087394 | A1 | 5/2003 | Sharma | |
| 2003/0235563 | A1 | 12/2003 | Strom | |
| 2003/0235580 | A1 | 12/2003 | Zhang | |
| 2004/0048372 | A1 | 3/2004 | Hariri | |
| 2004/0057938 | A1 | 3/2004 | Ghinelli | |
| 2004/0110287 | A1 | 6/2004 | Clarke | |
| 2004/0161419 | A1 | 8/2004 | Strom | |
| 2004/0170615 | A1 | 9/2004 | Soo | |
| 2005/0019865 | A1 | 1/2005 | Kihm | |
| 2005/0032209 | A1 | 2/2005 | Messina | |
| 2005/0037491 | A1 | 2/2005 | Mistry | |
| 2005/0054093 | A1 | 3/2005 | Haas | |
| 2005/0054098 | A1 | 3/2005 | Mistry | |
| 2005/0058629 | A1 | 3/2005 | Harmon | |
| 2005/0058631 | A1 | 3/2005 | Kihm | |
| 2005/0124003 | A1 | 6/2005 | Atala | |
| 2006/0078993 | A1 | 4/2006 | Phan | |
| 2006/0153816 | A1 | 7/2006 | Brown | |
| 2006/0153817 | A1 | 7/2006 | Kihm | |
| 2006/0153818 | A1 | 7/2006 | Dhanaraj | |
| 2006/0154366 | A1 | 7/2006 | Brown | |
| 2006/0154367 | A1 | 7/2006 | Kihm | |
| 2006/0166361 | A1 | 7/2006 | Seyda | |
| 2006/0188983 | A1 | 8/2006 | Harris | |
| 2006/0222634 | A1 | 10/2006 | Clarke | |
| 2006/0223177 | A1 | 10/2006 | Harris | |
| 2006/0233765 | A1 | 10/2006 | Messina | |
| 2006/0233766 | A1 | 10/2006 | Messina | |
| 2006/0234376 | A1 | 10/2006 | Mistry | |
| 2007/0009494 | A1 | 1/2007 | Mistry | |
| 2007/0014771 | A1 | 1/2007 | Mistry | |
| 2007/0015278 | A1 | 1/2007 | Li | |
| 2007/0036767 | A1 | 2/2007 | Mistry | |
| 2007/0231297 | A1 | 10/2007 | Smith et al. | |

FOREIGN PATENT DOCUMENTS

| WO | WO 00/73421 A2 | 6/2000 |
| WO | PCTSG2005000174 | 6/2005 |

OTHER PUBLICATIONS

El-Gazzaz G et al. 2010. Analysis of function and predictors of failure in women undergoing repair of Crohn's related rectovaginal fistula. J Gastrointest Surg. May 2010;14(5):824-29.*
Brivanlou A.H., et al., "Stem cells, Setting standards for human embryonic stem cells", Science, 2003. 300(5621): p. 913-6.
Miki, T., et al. "Stem Cell Characteristics of Amniotic Epithelial Cells", Stem Cells 2005; 23:1549-1559.
Tylki-Szymska, A., et al., Amniotic tissue transplantation as a trial of treatment in some lysosomal storage diseases. Journal of Inherited Metabolic Disease, 1985. 8(3): p. 1.
Wei, J., et al., "Human amnion-isolated cells normalize blood glucose in streptozotocin-induced diabetic mice". Cell Transplantation, 2003 vol. 12, pp. 545-552.
Terada, S., et al., "Inducing proliferation of human amniotic epithelial (HAE) cells for cell therapy", Cell Transplantaion, 2000, vol. 9, pp. 701-704.
Parolina, Ornella, et al., Stem Cells 2008;26:300-311.
Uchida et al. (2000) Neurotrophic function of conditioned medium from human amniotic epithelial cells. J. Neurosci. Res. 62:585-590.
Sun et al. (2003) Glucocorticoids induce cytosolic . . . J.Clin. Endocrinol. Metabol. 88(11):5564-5571.

(Continued)

*Primary Examiner* — Lora E Barnhart Driscoll
(74) *Attorney, Agent, or Firm* — Linda O. Palladino; Gail M. Kempler

(57) ABSTRACT

The invention is directed to methods related to surgery, for example gastrointestinal surgery. In particular, the invention is methods of treating fistulae, promoting accelerated healing of anastomoses and preventing failure of anastomoses. Such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone or in combination.

3 Claims, No Drawings

OTHER PUBLICATIONS

Marvin et al. (2002) Expression of angiogenic and neurotrophic factors in the human amnion and choriodecidua. Am. J. Obstet. Gynecol. 187(3):728-734.

Ihara et al, (1992) Wound closure in foetal rat skin. Development 114:573-82.

Ladwig, et al. (2002) Ratios of activated matrix metalloproteinase-9 to tissue inhibitor . . . Wound Rep Reg 10:26-37.

Robson, M.C. and Krizek, T.J. (1973) The effect of human amniotic membranes on the bacterial population of infected rat burns. Ann of Surg, 177:144-149.

Robson, M.C., et al., (1973) Quantitative comparison of biological dressings. Jour Surg Res 14:431-434.

Robson, M.C., et al., (1973) Amniotic membranes as a temporary wound dressing. Surgery, Ob & Gyn, 136:904-906.

Robson, M.C. and Krizek, T. J., (1974) Clinical experiences with amniotic membranes as a temporary biologic dressing. Connecticut Med 38:449-451.

Kucan, J.O., et al, (1982) Amniotic membranes as dressings following facial dermabrasion. Ann Plast Surg 8:523-527.

Wu, C-H, et al., (2003) Wound healing effects of porcine placental extracts on rats with thermal injury. British J Dermatol 148:236-245.

Koyano et al., (2002) Synthesis and release of activin and noggin by cultured human amniotic epithelial cells. Develop. Growth Differ. 44:103-112.

Tahara et al. (1995) Expression of messenger ribonucleic acid . . . J. Clin. Endocrinol. Metabol. 80:138-146.

Denison et al. (1998) Cytokine secretion by human fetal membranes, decidua and placenta at term. Hum. Reprod. 13:3560-3565.

* cited by examiner

METHODS RELATED TO SURGERY

CROSS-REFERENCE TO RELATED APPLICATIONS

This application claims priority under 35 USC §119(e) to U.S. Provisional Application No. 60/666,949, filed Mar. 31, 2005, U.S. Provisional Application No. 60/699,257, filed Jul. 14, 2005, U.S. Provisional Application No. 60/742,067, filed Dec. 2, 2005, and U.S. Provisional Application No. 60/958, 376, filed Jul. 5, 2007, and under 35 USC §120 to U.S. Utility application Ser. No. 11/333,849, filed Jan. 18, 2006 (now abandoned), U.S. Utility application Ser. No. 11/392,892, filed Mar. 29, 2006, and U.S. Utility application Ser. No. 11/724,094, filed Mar. 14, 2007, the contents of which are incorporated herein by reference in their entirety.

FIELD OF THE INVENTION

The field of the invention is methods related to surgery, in particular, gastrointestinal surgery. In particular, the field of the invention is methods of treating fistulae, promoting the accelerated healing of anastomoses and preventing failure of anastomoses. Such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone or in combination.

BACKGROUND OF THE INVENTION

Fistulae are abnormal communications between two epithelial-lined surfaces. While the most common fistulae are gut-to-gut fistulae, many other types of fistulae have been described in the medial literature. Gastrointestinal (GI) fistulae represent all abnormal communications that involve the alimentary tract and can be broadly divided into congenital or acquired GI fistulae. Congenital GI fistulae are embryonic in origin and include branchial, tracheoesophageal and omphalomesenteric fistulae. Acquired GI fistulae can be categorized as internal or external. Internal GI fistulae include intestinal (i.e. gut-to-gut) or extraintestinal (i.e. genitourinary) fistulae. External (also called cutaneous) GI fistulae are classified as high-output or low-output. In addition, there are Complex Acquired GI fistulae which involve an internal and external component, surgically created fistulae and GI sinus tracts, which are attached to the alimentary canal at one end but then end blindly at the other end. (Pickhardt, P. J., et al., Radiology 2002 224(1): 9-23)

Major causes of GI fistulae include inflammation (i.e. Crohn's Disease, diverticulitis, infection, cholecystitis, appendicitis, pancreatitis); surgery/iatrogenic injury; malignancy; radiation; aortic aneurysm/graft; peptic ulcer disease; trauma; ischemia; foreign bodies; and idiopathic. (Pickhardt, P. J., et al., Radiology 2002 224(1): 9-23).

Treatments for fistulae vary widely, depending upon the cause, the anatomical structures involved and the general health of the patient. In some instances surgery may be required to treat the fistula (i.e. fistulae caused by inflammation). In most instances, however, conservative medical management is considered first. Such medical management generally includes extended hospital stays and intensive medical attention aimed at maintaining fluid and electrolyte balance, providing bowel rest and nutrition support, initiating medication treatment, ensuring skin protection and containing the fistula effluent. (Pontieri-Lewis, V., Medsurg Nursing, 2005, 14(1):68-72). Consequently, conservative medical management is an expensive course of treatment.

An anastomosis is created when the two cut ends of any hollow organs are sutured or stapled together, usually to restore continuity after resection or to bypass an unresectable disease process. Anastomoses are typically performed on blood vessels (e.g. coronary artery bypass); GI tract (e.g. resections of gastrointestinal organs are followed by anastomosis to restore continuity; bariatric surgery); urinary tract (e.g. radical cystectomy); microsurgery, e.g. so-called "nerve anastomosis" (not strictly an anastomosis according to the above definition).

Fashioning an anastomosis is typically a complex and time-consuming step in a surgical operation, but almost always crucial to the outcome of the procedure.

BRIEF SUMMARY OF THE INVENTION

The compositions described herein have previously been shown to be useful in treating wounds and preventing incisional hernia formation (see US Publication No. 2006-0222634-A1 and US Publication No. 2007-0231297, which are incorporated herein by reference). It is an object of the instant invention to provide novel methods for treating fistulae, and in particular, GI fistulae, especially following surgical intervention to treat such fistulae. It is further an object of the instant invention to provide improved and accelerated healing of anastomoses as well as decreasing anastomosis failure, for example, such as that seen in bariatric surgery. Such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone and/or in combination with each other and/or with other agents including active and/or inactive agents and with other therapies. The data contained herein describes the successful use of the compositions of the present invention for the treatment of wounds. The cellular processes involved in such wound healing are mediated or modulated by humoral substances including but not limited to cytokines, lymphokines, growth factors, and hormones (see complete definition set forth above). Because the novel compositions described herein improve the healing of connective, epithelial, nervous and muscle tissue injured during surgery, they are equally useful for healing internal organs, such as, for example, intestines and blood vessels, as they are for healing cutaneous and fascial structures.

Accordingly, a first aspect of the invention is a method for treating fistulae in a patient in need thereof comprising administering to the patient a therapeutically effective amount of one or more compositions comprising ECS cells, conditioned media derived therefrom, cell lysate derived therefrom or cell products derived therefrom. One embodiment is a method wherein the treatment occurs during surgical intervention to treat the fistulae.

A second aspect of the invention is a method for promoting accelerated healing of anastomoses in a patient in need thereof comprising administering to the patient a therapeutically effective amount of one or more compositions comprising ECS cells, conditioned media derived therefrom, cell lysate derived therefrom or cell products derived therefrom.

One embodiment is a method wherein the treatment occurs during surgery to create the anastomosis.

A third aspect of the invention is a method for preventing failure of anastomoses in a patient in need thereof comprising administering to the patient a therapeutically effective amount of one or more compositions comprising ECS cells, conditioned media derived therefrom, cell lysate derived therefrom or cell products derived therefrom. One embodiment is a method wherein the treatment occurs during surgery to create the anastomosis.

In certain embodiments the ECS cells are AMP cells. In a particular embodiment the AMP cells are pooled AMP cells. In another particular embodiment the conditioned media is ACCS. And in still another particular embodiment the ACCS is pooled ACCS.

A fourth aspect of the invention is one in which the ECS cells are partially differentiated or fully differentiated. In one embodiment the ECS cells are AMP cells and the AMP cells are partially differentiated or fully differentiated. In other embodiments a mixture of undifferentiated, partially differentiated or fully differentiated AMP cells are used in practicing the methods of the invention.

A fifth aspect of the invention is one in which the ECS cells, including AMP cells, conditioned media derived therefrom, cell lysate derived therefrom or cell products derived therefrom are administered in combination with other agents or therapies. In one embodiment of this aspect of the invention the other agents are active agents.

Other features and advantages of the invention will be apparent from the accompanying description, examples and the claims. The contents of all references, pending patent applications and published patents, cited throughout this application are hereby expressly incorporated by reference. In case of conflict, the present specification, including definitions, will control.

Definitions

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristic of secreting a unique combination of physiologically relevant cytokines in a physiologically relevant temporal manner into the extracellular space or into surrounding culture media. In one embodiment, the ECS cells secrete at least one cytokine selected from VEGF, Angiogenin, PDGF and TGFβ2 and at least one MMP inhibitor selected from TIMP-1 and TIMP-2. In another embodiment, the ECS cells secrete more than one cytokine selected from VEGF, Angiogenin, PDGF and TGFβ2 and more than one MMP inhibitor selected from TIMP-1 and TIMP-2. In a preferred embodiment, the ECS cells secrete the cytokines VEGF, Angiogenin, PDGF and TGFβ2 and the MMP inhibitors TIMP-1 and TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666,949, 60/699,257, 60/742,067, U.S. Provisional Application No. 60/813,759, U.S. application Ser. No. 11/333,849, U.S. application Ser. No. 11/392,892, and PCTUS06/011392, each of which is incorporated herein in its entirety).

By the term "animal-free" when referring to certain compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized.

As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "amnion-derived cellular cytokine solution" or "ACCS" means conditioned medium that has been derived from AMP cells or expanded AMP cells. "Amnion-derived cellular cytokine solution" or "ACCS" has previously been called "amnion-derived cellular cytokine suspension".

The term "physiological level" as used herein means the level that a substance in a living system is found and that is relevant to the proper functioning of a biochemical and/or biological process.

As used herein, the term "pooled" means a plurality of compositions that have been combined to create a new composition having more constant or consistent characteristics as compared to the non-pooled compositions. For example, pooled ACCS have more constant or consistent characteristics compared to non-pooled ACCS.

The term "therapeutically effective amount" means that amount of a therapeutic agent necessary to achieve a desired physiological effect (i.e. promote healing of fistulae following surgical intervention).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulae, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scarring and/or the wounded area possesses tissue strength that is closer to that of uninjured tissue and/or the wounded tissue attains some degree of functional recovery.

As used herein, the term "fistula" means any abnormal communication between two epithelial-lined surfaces. The fistula may go from the body surface into a blind pouch or into an internal organ or go between two internal organs. Without limitation, fistulae may be congenital or acquired; internal or external or both; intestinal or extraintestinal.

As used herein, the term "anastomosis" means a surgical procedure wherein two cut ends of any hollow organs are sutured or stapled together.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses

Intestinal (gut-to-gut) fistulae are fistulae that begin and end on the alimentary canal. Common examples include gastrogastric fistulae, a common complication of gastric bypass surgery, and enteroenteric fistulae which generally form between two regions of the small intestine. The compositions and methods of the invention are useful in treating intestinal fistulae.

Genitourinary fistulae are abnormal communications between the urinary and genital tract. Fistulae of the genitourinary tract have diverse anatomic locations, causes, and clinical features. For example, they can involve the upper urinary tract (kidney, ureter), the lower urinary tract (bladder, urethra), or the female reproductive tract (vagina, uterus). Causes include infection, inflammatory disease, neoplasms, congenital conditions, trauma, and iatrogenic injury. Management approaches depend on the type of fistula, the degree of morbidity, and the overall functional status of the patient and vary from conservative observation to aggressive surgical repair. (Yu, N. C., et al., RadioGraphics, 2004, 24:1331-1352). The compositions and methods of the invention are useful in treating genitourinary fistulae.

Biliary fistulae are an established and abnormal communication between any portion of the biliary tree and some other area. The fistula may communicate with the exterior or with an internal cavity. Biliary fistulae are commonly caused by trauma and surgery, gallstones, peptic ulcers or neoplasm. The compositions and methods of the invention are useful in treating biliary fistulae.

Vascular fistulae are abnormal communications between two or more arteries, or between an artery and a vein. The compositions and methods of the invention are useful in treating vascular fistulae.

Respiratory fistulae are abnormal communications between the respiratory system and another system. An example of this type of fistula is a tracheoesophageal fistula (between trachea and esophagus) which is typically caused by malignancy. The compositions and methods of the invention are useful in treating respiratory fistulae.

External low-output and high-output fistulae (i.e. enterocutaneous fistula or rectovaginal fistula) involve the skin or another external surface epithelium. Enterocutaneous fistulae that drain less than 200 mL of fluid per day are known as low-output fistulae, whereas those that drain more than 500 mL of fluid per day are known as high-output fistulae (see Schwartz's Principles of Surgery, 8th Ed.). The compositions and methods of the invention are useful in treating external low-output and high-output fistulae.

Surgically created fistulae, e.g. arteriovenous fistulae for access for hemodialysis. The compositions and methods of the invention are useful in healing surgically created fistulae.

An anastomosis is created when the two cut ends of any hollow organs are sutured or stapled together. Anastomoses are typically performed on:

Blood vessels (arteries and veins): Most vascular procedures, including all arterial bypass operations (e.g. coronary artery bypass), aneurysmectomy (a surgical procedure performed to repair a weak area in the aorta), and all solid organ transplants require vascular anastomoses.

Gastrointestinal (GI) tract (esophagus, stomach, small bowel, large bowel, bile ducts, and pancreas). Virtually all elective resections of gastrointestinal organs are followed by anastomoses to restore continuity; pancreaticoduodenectomy (the Whipple procedure) is considered a massive operation, in part, because it requires three separate anastomoses (stomach, biliary tract and pancreas to small bowel). Bypass operations on the GI tract, once rarely performed, are the cornerstone of bariatric surgery. The widespread use of mechanical suturing devices (linear and circular staplers) changed the face of gastrointestinal surgery.

Urinary tract (ureters, urinary bladder, urethra). Radical prostatectomy and radical cystectomy both require anastomosis of the bladder to the urethra in order to restore continuity.

Microsurgery: The advent of microsurgical techniques has allowed anastomoses previously thought impossible, such as the so-called "nerve anastomoses" (not strictly an anastomosis according to the above definition), and operations to restore fertility after tubal ligation or vasectomy.

In addition to those listed above, all other types of anastomoses are contemplated by the methods of the invention as well.

Obtaining and Culturing of Cells

ECS—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666, 949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete a unique combination of cytokines into the extracellular space or into surrounding culture media. Suitable cells are those in which the cytokine or cytokines occurs in the physiological range of ~5.0-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2.

AMP cell compositions are prepared using the steps of a) recovery of the amnion from the placenta, b) dissociation of the cells from the amniotic membrane, c) culturing of the cells in a basal medium with the addition of a naturally derived or recombinantly produced human protein; d) selecting AMP cells from the cell culture, and optionally e) further proliferation of the cells, optionally using additional additives and/or growth factors. Details are contained in US Publication No. 2006-0222634-A1, which is incorporated herein by reference.

AMP cells are cultured as follows: The AMP cells are cultured in a basal medium. Such medium includes, but is not limited to, Epilife (Cascade Biologicals), Opti-pro, VP-SFM, IMDM, Advanced DMEM, K/O DMEM, 293 SFM II (all made by Gibco; Invitrogen), HPGM, Pro 293S-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. Details on this procedure are contained in US Publication No. 2006-0222634-A1, which is incorporated herein by reference.

In a most preferred embodiment, the cells are cultured using a system that is free of animal products to avoid xeno-contamination. In this embodiment, the culture medium is Stemline I or II, Opti-pro, or DMEM, with human albumin added up to concentrations of 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free. Details on this procedure are contained in US Publication No. 2006-0222634-A1, which is incorporated herein by reference.

In alternative embodiments, where the use of non-human serum is not precluded, such as for in vitro uses, the culture medium may be supplemented with serum derived from mammals other than humans, in ranges of up to 40%.

Additional proliferation—Optionally, other proliferation factors are used. In one embodiment, epidermal growth factor (EGF), at a concentration of between 0-1 µg/mL is used. In a preferred embodiment, the EGF concentration is around 10 ng/mL. Alternative growth factors which may be used include, but are not limited to, TGFα or TGFβ (5 ng/mL; range 0.1-100 ng/mL), activin A, cholera toxin (preferably at a level of about 0.1 µg/mL; range 0-10 µg/mL), transferrin (5 µg/mL; range 0.1-100 µg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation.

Generation of Conditioned Medium

ECS conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. Skilled artisans are familiar with cryopreservation, lyophilization, and sustained-release formulation methodologies.

The compositions of the invention can be prepared in a variety of ways depending on the intended use of the compositions. For example, a composition useful in practicing the invention may be a liquid comprising an agent of the invention, i.e. ECS cells, including AMP cells and/or ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like, suitable for topical administration.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions

The present invention provides pharmaceutical compositions of ECS cells, including AMP cells and/or ACCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits

The invention also provides for an article of manufacture comprising packaging material and a pharmaceutical composition of the invention contained within the packaging material, wherein the pharmaceutical composition comprises compositions of ECS cells, including AMP cells and/or ACCS. The packaging material comprises a label or package insert which indicates that the ECS cells, including AMP cells and/or ACCS can be used for preventing/treating fistulae, for example, GI fistulae.

Formulation, Dosage and Administration

Compositions comprising ECS cells, including AMP cells and/or ACCS may be administered to a subject to provide various cellular or tissue functions, for example, to prevent/treat fistulae, for example, GI fistulae. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in preventing/treating fistulae, for example, GI fistulae. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

One of skill in the art may readily determine the appropriate concentration, or dose, of the ECS cell conditioned media, including ACCS, for a particular purpose. The skilled artisan will recognize that a preferred dose is one which produces a therapeutic effect, such as treating fistulae, in a patient in need thereof. For example, one preferred dose of ACCS is in the range of about 0.1-to-1000 µL per square centimeter of applied area. Other preferred dose ranges are 1.0-100 µL per square centimeter of applied area and about 0.01-to-50.0 µL per square centimeter of applied area. Of course, proper doses of ECS cell conditioned media, including ACCS, will require empirical determination at time of use based on several variables including but not limited to the severity of disease, disorder or condition being treated; patient age, weight, sex, health; other medications and treatments being administered to the patient; and the like. One of skill in the art will also recognize that number of doses (dosing regimen) to be administered needs also to be empirically determined based on, for example, severity of disease, disorder or condition being treated. In a one embodiment, one dose is sufficient. Other embodiments contemplate, 2, 3, 4, or more doses. Furthermore, conditioned media derived from ECS cells, including ACCS derived from AMP cells, is typically administered at full strength because the cytokines and factors contained therein are present at physiologic levels suitable for the healing of injured and diseased cells and tissues (see Steed, D. L., et al, Eplasty 2008, Vol. 8, e19, published online Apr. 7, 2008, for a discussion of such physiologic levels of cytokines and factors in ACCS). Again, the volume of conditioned media, including ACCS, will depend upon the extent of injury or disease being treated, etc., and can only be determined by the attending physician at time of use.

One of skill in the art may readily determine the appropriate concentration, or dose, of the ECS cells, including AMP cells, for a particular purpose, as well. The skilled artisan will recognize that a preferred dose is one which produces a therapeutic effect, such as treating fistulae, in a patient in need thereof. For example, ECS cells, including AMP cells, are prepared at a concentration of between about $1\times10^7$-$1\times10^8$ cells/mL, preferably at about $2.5\times10^7$-$7.5\times10^7$ cells/mL, and most preferably at about $5\times10^7$ cells/mL. The volume of cell mixture administered will depend upon several variables and can only be determined by the attending physician at time of use. Such proper doses of the ECS cells, including AMP cells, will require empirical determination based on such variables as the severity and type of disease, injury, disorder or condition being treated; patient age, weight, sex, health; other medications and treatments being administered to the patient; and the like.

The present invention provides a method of preventing/treating fistulae, for example, GI fistulae, by administering to a subject ECS cells, including AMP cells and/or ACCS in a therapeutically effective amount. By "therapeutically effective amount" is meant the dose of ECS cells, including AMP cells and/or ACCS that is sufficient to elicit a therapeutic effect. Thus, the concentration of ECS cells, including AMP cells and/or ACCS in an administered dose unit in accordance with the present invention is effective in preventing/treating fistulae, for example, GI fistulae.

In further embodiments of the present invention, at least one additional agent may be combined with the ECS cells, including AMP cells and/or ACCS. Such agents include active agents and/or inactive agents. Active agents include but are not limited to growth factors, cytokines, chemokines, antibodies, antibiotics, anti-fungals, anti-virals, other cell types, and the like. Inactive agents include carriers, diluents, stabilizers, gelling agents, delivery vehicles, ECMs (natural and synthetic), scaffolds, and the like. When the ECS cells, including AMP cells and/or ACCS are administered conjointly with other pharmaceutically active agents even less of the ECS cells, including AMP cells and/or ACCS may be needed to be therapeutically effective.

The timing of administration of ECS cells, including AMP cells and/or ACCS will depend upon the type and severity of the condition being treated. In a preferred embodiment, the ECS cells, including AMP cells and/or ACCS, are administered as soon as possible after surgery. In other preferred embodiments, the ECS cells, including AMP cells and/or ACCS are administered more than one time following surgery. Timing of treatment and administration of the compositions of the invention is also dependent upon the severity and type of surgery being treated. For example, it may be advantageous to treat, or prime, the surgical site prior to surgery. It may also be advantageous to treat the surgical site post-surgery. It may also be advantageous to treat the surgical site during surgery, such as during surgical intervention to treat fistulae. Other embodiments contemplate different dosing intervals (i.e. prior to surgery and/or during surgery and/or after surgery).

ECS cells and/or conditioned media derived therefrom and/or cell lysates derived therefrom and/or cell products derived therefrom, including AMP cells, and/or ACCS and/or cell lysates derived therefrom and/or cell products derived therefrom can be administered by injection into a target site of a subject, preferably via a delivery device, such as a tube, e.g., catheter. In a preferred embodiment, the tube additionally contains a needle, e.g., a syringe, through which the cells and/or ACCS can be introduced into the subject at a desired location. Specific, non-limiting examples of administering cells to subjects may also include administration by subcutaneous injection, intramuscular injection, or intravenous injection. For example, if administration is intravenous, an injectable liquid suspension of AMP cells and/or ACCS and/or lysates and/or cell products derived therefrom can be prepared and administered by a continuous drip or as a bolus.

ECS cells and/or conditioned media derived therefrom and/or cell lysates derived therefrom and/or cell products derived therefrom, including AMP cells, and/or ACCS and/or cell lysates derived therefrom and/or cell products derived therefrom may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating compositions as described herein, in a pharmaceutically acceptable carrier or diluent and, as required, other ingredients enumerated above, followed by filter sterilization.

Alternatively, ECS cells including AMP cells may be transplanted into the recipient where the cells will proliferate and differentiate to form new cells and tissues thereby providing the physiological processes normally provided by that tissue, or may produce factors that cause the migration and/or differentiation of cells in the area of the transplant. Tissues are an aggregation of similarly specialized cells united in the performance of a particular function. Tissue is intended to encompass all types of biological tissue.

Support matrices into which the ECS cells and/or conditioned media derived therefrom and/or cell lysates derived therefrom and/or cell products derived therefrom, including AMP cells, and/or ACCS and/or cell lysates derived therefrom and/or cell products derived therefrom can be incorporated or embedded include matrices which are recipient-compatible and which degrade into products which are not harmful to the recipient. These matrices provide support and protection for ECS cells including AMP cells in vivo and are, therefore, the preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that bioactive compounds can be incorporated directly into the support matrix so that they are slowly released as the support matrix degrades in vivo. As the cell-polymer structure is vascularized and the structure degrades, ECS cells including AMP cells, may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immuno-modulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, ECS cells and/or conditioned media derived therefrom and/or cell lysates derived therefrom and/or cell products derived therefrom, including AMP cells, and/or ACCS and/or cell lysates derived therefrom and/or cell products derived therefrom may be transplanted or otherwise administered in a gel matrix (such as Gelfoam from Upjohn Company) which polymerizes to form a substrate in which the cells can grow or from which conditioned media, including ACCS, can be released over time. A variety of encapsulation technologies have been developed (e.g. Lacy et al., Science 254:1782-84 (1991); Sullivan et al., Science 252: 718-712 (1991); WO 91/10470; WO 91/10425; U.S. Pat. Nos. 5,837,234; 5,011,472; 4,892,538). During open surgical procedures involving direct physical access to the damaged tissue and/or organ, for example when treating fistulae, ECS cells and/or conditioned media derived therefrom, including AMP cells, and/or ACCS, delivery preparations are available options. The compositions can be repeatedly transplanted or otherwise administered at intervals until a desired therapeutic effect is achieved. The ECS cells, including AMP cells, may be undifferentiated, partially differentiated, fully differentiated, or a composition comprising a combination of undifferentiated, partially differentiated, fully differentiated ECS cells, including AMP cells.

The present invention also relates to the use of ECS cells including AMP cells in three dimensional cell and tissue culture systems to form structures analogous to tissue counterparts in vivo. The resulting tissue will survive for prolonged periods of time, and perform tissue-specific functions following transplantation into the recipient host. Methods for producing such structures are described in U.S. Pat. Nos. 5,624,840 and 6,428,802, which are incorporated herein in their entireties.

The three-dimensional matrices to be used are structural matrices that provide a scaffold for the cells, to guide the process of tissue formation. Scaffolds can take forms ranging from fibers, gels, fabrics, sponge-like sheets, and complex 3-D structures with pores and channels fabricated using complex Solid Free Form Fabrication (SFFF) approaches. Cells cultured on a three-dimensional matrix will grow in multiple layers to develop organotypic structures occurring in three dimensions such as ducts, plates, and spaces between plates that resemble sinusoidal areas, thereby forming new tissue. Thus, in preferred aspects, the present invention provides a scaffold, multi-layer cell and tissue culture system. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

Examples of such scaffolds include a three-dimensional stromal tissue or living stromal matrix which has been inoculated with stromal cells that are grown on a three dimensional support. The extracellular matrix proteins elaborated by the stromal cells are deposited onto the scaffold, thus forming a living stromal tissue. The living stromal tissue can support the growth of ECS cells including AMP cells or partially or fully differentiated cells (or combinations thereof) later inoculated to form the three-dimensional cell culture. Examples of other three dimensional scaffolds are described in U.S. Pat. No. 6,372,494.

The design and construction of the scaffolding to form a three-dimensional matrix is of primary importance. The matrix should be a pliable, non-toxic, injectable porous template for vascular ingrowth. The pores should allow vascular ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

A sponge-like structure can also be used to create a three-dimensional framework. The structure should be an open cell sponge, one containing voids interconnected with the surface of the structure, to allow adequate surfaces of attachment for sufficient ECS cells including AMP cells or partially or fully differentiated cells (or combinations thereof) to form a viable, functional implant.

The invention also provides for the delivery of ECS cells including AMP cells, including AMP cell compositions described herein, in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, ECS cells including AMP cells may be grown on such membranes, added to the membrane in either an undifferentiated, partially differentiated or fully differentiated form, or ACCS or cell lysates may be added to such membranes. Alternatively, amniotic tissue in which AMP cells have not been stripped away may be used to deliver ECS cells including AMP cells to a particular site. In all cases, ECS cells including AMP cells used in conjunction with amniotic tissue or other matrices can be used in combination with other therapeutically useful cells and/or cells expressing biologically active therapeutics such as those described in below.

Also contemplated by the methods of the invention are compositions comprising partially or fully differentiated ECS cells, including AMP cells. Such partially or fully differentiated cell compositions are obtained by treating ECS cells, including AMP cells, with appropriate reagents and under appropriate conditions wherein the cells undergo partial or complete differentiation. Skilled artisans are familiar with conditions capable of effecting such partial or complete differentiation. The cells may be treated under differentiating conditions prior to use (i.e. transplantation, administration, etc.), simultaneously with use or post-use. In certain embodiments, the cells are treated under differentiation conditions before and during use, during and after use, before and after use, or before, during and after use.

Skilled artisans will recognize that any and all of the standard methods and modalities for treating fistulae, for example, GI fistulae, or for healing anastomoses or preventing failure of anastomoses currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Recovery of AMP cells—AMP cells were dissociated from starting amniotic membrane using the dissociation agents PXXIII, and trypsin. The average weight range of an amnion was 18-27 g. The number of cells recovered per g of amnion was about $10\text{-}15 \times 10^6$ for dissociation with PXXIII and $5\text{-}8 \times 10^6$ for dissociation with trypsin.

Method of obtaining selected AMP cells: Cells were plated immediately upon isolation from the amnion. After ~2 days in culture non-adherent cells were removed and the adherent cells were kept. This attachment to plastic tissue culture vessel is the selection method used to obtain the desired population of cells. Adherent and non-adherent AMP cells appear to have a similar cell surface marker expression profile but the adherent cells have greater viability and are the desired population of cells. Adherent AMP cells were cultured until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reach ~120,000-150,000 cells/cm$^2$, they were collected and cryopreserved. This collection time point is called p0 and all subsequent analyses are done with thawed p0 AMP cells.

Example 2

Generation of ACCS

The AMP cells of the invention can be used to generate ACCS. The AMP cells were isolated as described herein and $1 \times 10^6$ cells/mL were seeded into T75 flasks containing 10 mL culture medium. The cells are cultured until confluent, the medium is changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention. It is also contemplated by the instant invention that the ACCS be cryopreserved following collection. It is also contemplated that the ACCS be lyophilized following collection.

Example 3

Detection of Growth Factors and Cytokines Important in Treating Fistulae, Healing Anastomosis and Preventing Anastomosis Failure To determine which growth factors and/or cytokines important in treating fistulae, healing anastomosis and preventing anastomosis failure may be secreted by the AMP cells of the present invention, ACCS was isolated from cell cultures that were seeded onto tissue culture treated flasks at a density of ~40,000 cells per cm². Cells were cultured in a proprietary serum-free medium supplemented with 10 ng/mL of EGF. Culture media was exchanged every 2 days during the growth period. After cells reached near confluency (~1-2 wk after isolation), fresh media was applied and ACCS was collected after three days and stored at −80° C. for subsequent analysis.

ACCS was analyzed for secreted factor content via antibody arrays, ELISA, multiplex assays and mass spectroscopy.

Results—The following relevant factors were detected in ACCS: VEGF, PDGF, Angiogenin, TGFβ2, TIMP-1 and TIMP-2. Thymosin β4 was detected by mass spectroscopy.

Example 4

Evaluation of Accelerated Wound Strength and Prevention of Acute Wound Failure Using ACCS One object of the invention is to decrease wound failure in surgical and traumatic injuries by treating these acute wounds with ACCS from AMP cells.

Art-accepted animal models for evaluating wound strength and wound failure (Robson, et al: The effect of cytokine growth factors on the prevention of acute wound failure. Wound Rep Regen 12: 38-43, 2004. Franz, et al: Fascial incisions heal faster than skin: A new model for abdominal wall repair. Surgery 129: 203-208, 2001) were used in experiments to assess whether or not ACCS could increased wound strength and decrease wound failure.

The animals were randomly assigned into one of 12 Groups. In Experimental Designs 1 and 2, each of the three animal models (Sham laparotomy, Healing laparotomy and Hernia) were treated with four experimental conditions of ACCS containing the humoral products of AMP cells. (No treatment, Control AMP cell media (0% conditioned), 50% ACCS and 100% ACCS). 100 IU of media is delivered to the site of the laparotomy myofascial and skin incisions prior to wounding.

Results: The application of ACCS resulted in a statistically significant increase in breaking strength (=p<0.05) (16.7 N) at Day 7 as compared to PBS (8 N) and UCM (10.5 N) in this animal model of wound failure. In addition, in this same animal model, the addition of ACCS resulted in a statistically significant increase in tensile strength (=p<0.05) (0.34 N/mm²) at Day 7 as compared to PBS (0.21 N/mm²) and UCM (0.23 N/mm²). These data indicate that ACCS is capable of increasing wound strength in this model.

Results obtained in the incisional hernia model: In the treatment group in which the incisions were "primed" with 100 μl ACCS only 25% of the animals formed incisional hernias, as compared to PBS or UCM (control groups) in which 100% of the animals developed incisional hernias. Furthermore, when the hernias were removed and their size measured, the ACCS treated group had an average hernia size that was ⅛ the size of the PBS treated controls and ½₁₂ the size of UCM controls. In addition, In the ACCS treated incision there is no visible indication of the incisional wound, whereas in the UCM treated incision, there is an obvious visible suture line. A histological section through the surgical site in both an UCM treated and the ACCS treated animal reveals that in the ACCS treated specimen, there is thick, organized fascia (F), an organized and intact rectus muscle (RM) and a well healed peritoneum (P). These features are not evident in the UCM treated specimen. Taken together, these data clearly demonstrate that the application of ACCS prior to incisional injury can increase wound strength, decrease or prevent wound failure as evidenced by both reduced rate of hernia formation and hernia size, and accelerate wound healing.

Histology: Histological analyses of provisional matrix structure, fibroblast migration, inflammatory response and wound angiogenesis is used to compare the groups using H&E and trichrome staining of samples are collected from laparotomy wounds or incisional hernias from rats. The density of wound collagen formation is measured using antibodies specific for rat collagen types I and III (Chemicon International, Inc., Temecula, Calif.). Cellular infiltration into the wounds at each time-point is measured as the mean cell number from three high-powered fields by a blinded observer using a microscope. In addition, histological specimens are digitized using a UMAX Astra 1200S scanner and analyzed using the computer software application Adobe PhotoShop version 5.0. Differences in cellularity and intensity of collagen staining are compared using the Students t test (SigmaStat, Jandel).

Example 5

Evaluation of Accelerated Wound Strength and Prevention of Acute Wound Failure Using AMP Cells Again, art-accepted animal models for evaluating wound strength and wound failure (Robson, et al: The effect of cytokine growth factors on the prevention of acute wound failure. Wound Rep Regen 12: 38-43, 2004. Franz, et al: Fascial incisions heal faster than skin: A new model for abdominal wall repair. Surgery 129: 203-208, 2001) were used in experiments to assess whether or not ACCS could increased wound strength and decrease wound failure.

Two groups were studied: 1) a normal saline-treated control abdominal wall group (NS) and a normal saline-washed, human AMP cell-primed abdominal wall group (AMP). In the NS group, the midline of the abdominal wall (the linea alba) was injected for 5 cm with 200 μL NS (priming). In the AMP group, 200 μL NS containing $1 \times 10^6$ AMP cells was also injected along the linea alba for 5 cm. After 5 minutes, the laparotomy incision was made and repaired as described (Wound Rep Regen 12: 38-43, 2004. Franz, et al: Fascial incisions heal faster than skin: A new model for abdominal wall repair. Surgery 129: 203-208, 2001). On post-operation day (POD) 7, 14 and 28, the rats were euthanized and isolated abdominal wall muscle and tendon strips and fresh biopsies of the abdominal wall-healing interface were collected for mechanical and histological testing.

Results: Tensiometric analysis was performed on uniform abdominal strips with the line of tissue deformation directly perpendicular to the linea alba/incision line. The AMP cell-treated tissue developed increased breaking strength in POD 7 incisions. The scar harvested on POD 7 showed evidence of higher vascularization, more granulation tissue, and organized fibro-proliferation in the AMP cell treated group as compared to the NS group.

Hernia model—To test whether AMP cells improved laparotomy healing and hernia formation, a rat hernia model (Dubay, D. A., et al, Ann Surg, 2007;245(1):140-146) was treated with AMP cells. $1\text{-}5 \times 10^6$ AMP cells in 200 μL NS or 200 μL NS were delivered on the linea alba over a 5 cm length. A 5 cm fascial laparotomy incision was made and closed with two fast absorbing suture stitches resulting in an intentional incisional hernia model. On POD 28, all rats were euthanized and the abdominal wall collected for hernia or wound defect assessment and size measurement.

Results—The hernia or wound size in the AMP cell-treated group was significantly smaller than those on the NS-treated group ($0.82\pm0.16$ cm$^2$ versus $2.72\pm0.56$ cm$^2$). Morphology of hernia ring showed there was more vascularization within the hernia ring from the AMP cell-treated group compared to NS group, suggesting accelerated healing and improved laparotomy wound repair in the AMP cell-treated group.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for accelerating the rate of healing of a surgically created anastomosis in a treated patient compared to the rate of healing in an untreated patient, the method comprising the step of administering by injection directly to the anastomosis at the time the anastomosis is surgically created between 0.1-to-1000 μL per square centimeter of applied area a composition comprising Amnion-derived Cellular Cytokine Solution (ACCS) or pooled ACCS wherein the ACCS or pooled ACCS contains physiologic concentrations of VEGF, TGFβ2, Angiogenin, PDGF, TIMP-1 and TIMP-2, and wherein the physiologic concentration is about 5.0-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1 and about 1.04 μg/mL for TIMP-2.

2. The method of claim 1 wherein the ACCS or pooled ACCS is administered in combination with other agents or therapies.

3. The method of claim 1 wherein the anastomosis is created surgically by suturing or stapling the two cut ends of a hollow organ, wherein the hollow organ having the two cut ends is selected from the group consisting of a blood vessel, a gastrointestinal tract, and a urinary tract.

* * * * *